US006489449B2

(12) United States Patent
Yu et al.

(10) Patent No.: US 6,489,449 B2
(45) Date of Patent: Dec. 3, 2002

(54) PEPTIDES FOR INHIBITION OF HIV INFECTION

(75) Inventors: Yeon Gyu Yu, Seoul (KR); Key-Sun Kim, Seoul (KR); Bong-Suk Jin, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/834,628

(22) Filed: Apr. 16, 2001

(65) Prior Publication Data

US 2002/0119922 A1 Aug. 29, 2002

(30) Foreign Application Priority Data

Nov. 6, 2000 (KR) .............................. 00-65664

(51) Int. Cl.[7] ......................... C07K 16/00; A61K 38/00
(52) U.S. Cl. ................... 530/388.35; 530/324
(58) Field of Search ............................ 530/324, 388.35

(56) References Cited

PUBLICATIONS

Berger, HIV entry and tropism: the chemokine receptor connection, AIDS 11(suppl A):S3–S16 (1997).
Doranz et al., Chemokine receptors as fusion cofactors for human immunodeficiency virus type 1 (HIV–1), Immunologic Research 16:15–28 (1997).
Moore et al., Co–receptors for HIV–1 entry, Current Opinion in Immunology 9(4):551–562 (1997).
Chan et al., HIV entry and its inhibition, Cell, 93:681–684 (1998).
Judice et al., Inhibition of HIV type 1 in infectivity by constrained α–helical peptides: implications for the viral fusion mechanism, Prop. Natl. Acad. Sci. USA 94:13426–13430 (1997).
Ryu et al., Development for an in vitro assay system for screening of gp41 inhibitory compounds, Molecules and Cells 8(6):717–723 (1998).
Woo et al., Inhibition of gp 120–CD4 interaction by various plant extracts, Phytomedicine 4:53–58 (1997).
Lawless et al., HIV–1 Membrane Fusion Mechanism: Structural Studies of the Interactions Between Biologically–active Peptides from gp41, Biochemistry 35:13697–13708, at 13705 (1996).
Rimsky et al., Determinants of Human Immunodeficiency Virus Type 1 Resistance to gp41–Derived Inhibitory Peptides, Journal of Virology 72:986–993 (1998).
Wild et al., Peptides Corresponding to Predictive α–Helical Domain of Human Immunodeficiency Virus Type 1 gp41 are Potent Inhibitors of Virus Infection, PNAS 91:9770–9774 (1994).

*Primary Examiner*—Hankyel T. Park
(74) *Attorney, Agent, or Firm*—Finnegan, Henderson, Farabow, Garrett & Dunner, L.L.P.

(57) ABSTRACT

The present invention relates to peptides that can inhibit the infection of HIV, and more particularly, to peptides consisting of less than 30 amino acids which can introduce a helix capping motif into a peptide derived from C-terminal helical region (its 628–646th amino acid region) of gp41, an envelope glycoprotein of HIV, as well as consisting of the symmetrical bivalent peptide through the introduction of a branched amino acid, Fmoc-Lys(Fmoc)-OH at C-terminus of its peptide, and induce a more stable helical structure thus inhibiting the infection of HIV.

4 Claims, 11 Drawing Sheets

SEQUENCE LISTING

<160> NUMBER OF SEQ ID NOS: 13

<210> SEQ ID NO 1
<211> LENGTH: 36
<212> TYPE: PRT
<213> ORGANISM: Artificial Sequence
<220> FEATURE:
<223> OTHER INFORMATION: Description of Artificial Sequence: Synthetic peptide
<223> OTHER INFORMATION: DP178

<400> SEQUENCE: 1

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: Helix-capping Motif

<400> SEQUENCE: 2

Ala Pro Lys Glu
 1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: Helix-capping Motif

<400> SEQUENCE: 3

Lys Gln Gly Ile
 1

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: WT

<400> SEQUENCE: 4

Trp Met Glu Trp Asp Arg Glu Ile Asn Asn Tyr Thr Ser Leu Ile His
 1               5                  10                  15

Ser Leu Ile

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: MT

<400> SEQUENCE: 5

Trp Met Ala Trp Ala Arg Glu Ile Ala Ala Tyr Ala Lys Leu Ile Ala
 1               5                  10                  15

Ala Leu Ile

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: MT*

<400> SEQUENCE: 6

Trp Met Glu Trp Asp Ala Glu Ile Ala Ala Tyr Thr Glu Leu Ile Ala
 1               5                  10                  15
Ala Leu Ile

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: Ncap-MT

<400> SEQUENCE: 7

Ala Pro Lys Glu Trp Met Ala Trp Ala Arg Glu Ile Ala Ala Tyr Ala
 1               5                  10                  15
Lys Leu Ile Ala Ala Leu Ile
            20

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: Caps-WT

<400> SEQUENCE: 8

Ala Pro Lys Glu Trp Met Glu Trp Asp Arg Glu Ile Asn Asn Tyr Thr
 1               5                  10                  15
Ser Leu Ile His Ser Leu Ile Lys Gln Gly Ile
            20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: Caps-MT

<400> SEQUENCE: 9

Ala Pro Lys Glu Trp Met Ala Trp Ala Arg Glu Ile Ala Ala Tyr Ala
 1               5                  10                  15
Lys Leu Ile Ala Ala Leu Ile Lys Gln Gly Ile
            20                  25

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: Caps-MT*

<400> SEQUENCE: 10

Ala Pro Lys Glu Trp Met Glu Trp Asp Ala Glu Ile Ala Ala Tyr Thr
 1               5                  10                  15
Glu Leu Ile Ala Ala Leu Ile Lys Gln Gly Ile
            20                  25

```
<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: NCap-MT*[BG1]
<221> NAME/KEY: MOD_RES
<222> LOCATION: (25)
<223> OTHER INFORMATION: Fmoc-Lys(Fmoc)-OH

<400> SEQUENCE: 11

Ala Pro Lys Glu Trp Met Glu Trp Asp Ala Glu Ile Ala Ala Tyr Thr
 1               5                  10                  15

Glu Leu Ile Ala Ala Leu Ile Gly Lys
            20                  25

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: Ncap-MT*[BG2]
<221> NAME/KEY: MOD_RES
<222> LOCATION: (26)
<223> OTHER INFORMATION: Fmoc-Lys(Fmoc)-OH

<400> SEQUENCE: 12

Ala Pro Lys Glu Trp Met Glu Trp Asp Ala Glu Ile Ala Ala Tyr Thr
 1               5                  10                  15

Glu Leu Ile Ala Ala Leu Ile Gly Gly Lys
            20                  25

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: Ncap-MT*[BG3]
<221> NAME/KEY: MOD_RES
<222> LOCATION: (27)
<223> OTHER INFORMATION: Fmoc-Lys(Fmoc)-OH

<400> SEQUENCE: 13

Ala Pro Lys Glu Trp Met Glu Trp Asp Ala Glu Ile Ala Ala Tyr Thr
 1               5                  10                  15

Glu Leu Ile Ala Ala Leu Ile Gly Gly Gly Lys
            20                  25
```

PEPTIDES FOR INHIBITION OF HIV INFECTION

BACKGROUND OF THE INVENTION

1. Field of the Invention

The present invention relates to peptides that can inhibit the infection of HIV, and more particularly, to peptides consisting of less than 30 amino acids which can introduce a helix capping motif into a peptide derived from C-terminal helical region (its 628–646$^{th}$ amino acid region) of gp41, an envelope glycoprotein of HIV, as well as consisting of the symmetrical bivalent peptide through the introduction of a branched amino acid, Fmoc-Lys(Fmoc)-OH at C-terminus of its peptide, and induce a more stable helical structure thus inhibiting the infection of HIV.

2. Description of the Related Art

Host cell infection by HIV is mediated by the binding between envelope glycoproteins of HIV and receptors of a host cell such as CD4 and chemokine receptors (Berger, AIDS, 11, S3-16, 1997; Doranz et al., Immunol. Res., 16, 15–28, 1997; Moore et al., Current Opin. Immunol., 9, 551–562, 1997). When gp120 of HIV binds CD4 of a host cell, gp120 undergoes a structural change so that it can bind a chemokine receptor in a host cell. Once the binding is completed, a hydrophobic amino terminal fusion peptide region of gp41 of HIV can be inserted in the membrane of a host cell. Then, three gp41 envelope glycoproteins form a six-stranded a-helical bundle, in which three N-peptides associate to form the central trimeric coiled-coil and three C-peptides pack obliquely in an antiparalllel manner on the surface of the coiled-coil core. This bundle structure is involved in a fusion between HIV cell membrane and a host cell membrane as a result thus enabling the core of HIV to penetrate into the cytoplasm of a host cell (Chan and Kim, Cell, 93, 681–684, 1998). Gp41, a glycoprotein present on the envelope of HIV, is also involved in the fusion between HIV envelope and human cell membrane. Gp41 consists of a fusion peptide which exhibits an activity on cell membrane fusion, an N-terminal helical region, a C-terminal helical region, a transmembrane region, and a cytoplasmic region. Peptides derived from N- and C-helical region of the extracellular domain of gp41 can bind to each other in an aqueous solution due to their strong interactions and thus form a very stable complex consisting of six helices from three N-peptides and three C-peptides. The above interaction between the two helical regions is known to play a crucial role in the activity of cell fusion as well as the structural stability of gp41 protein itself. Therefore, it becomes obvious form the above that any substance that can inhibit the above interaction between the two helical regions will be able to inhibit the stability as well as the function of gp41, which will eventually lead to the inhibition of HIV infection thus becoming a promising therapeutic agent for AIDS treatment. In particular, hydrophobic interactions among three nonpolar residues ($Trp_{628}$, $Trp_{631}$, and $Ile_{635}$ of gp41) of C34 peptide (the 628$^{th}$–661$^{st}$ amino acid) derived from C-terminus of gp41 and a cavity formed by C-terminal portion of the coiled-coil core are known to be important in antiviral activities. These structural features imply that the formation of a helical structure is a prerequisite for the binding between a C-peptide and an N-terminal helical region. DP178, a 36-mer peptide(638$^{th}$–673$^{rd}$ amino acid, SEQ ID NO.1: YTSLIHSLIEESQNQQEKNEQELLELDKWASLWNWF) derived from C-terminal helical region of gp41 is also known to inhibit gp41-mediated cell fusion, and 1 ng/mL of DP178 has about 90% inhibitory activity on cell fusion mediated by gp41. DP178 is known to inhibit cell fusion by binding an N-terminal helical region of gp4l thus preventing its interaction with the C-terminal helical region of gp41. DP178 and its modified peptides having an antiviral activity consisted of at least 34–36 amino acids and they did not form a secondary structure in an aqueous solution. However, when the i$^{th}$ and the (i+7)$^{th}$ amino acid residues of a peptide consisting of 27 amino acids derived from C-terminus of gp41 without an antiviral activity are chemically cross-linked, the above peptide formed a helical structure and showed an antiviral activity. Hence, helical stabilization of the C-peptides appears to be an important factor in promoting binding affinity for the coiled-coil motif of gp41 as well as for anti-HIV activity(Judice, Proc. Natl. Acd. Sci. USA, 94,13426–13430, 1997).

However, thus obtained peptides have drawbacks as specified below. First, a peptide should have at least 30 amino acids to be able to inhibit gp41-mediated cell fusion and this incurs a lot of expense in synthesizing those peptides. Second, there requires an additional method to chemically link amino acid residues in order to obtain a peptide with a helical structure or a bivalent sequence. Therefore, it has been a long-felt need to develop a peptide with an antiviral activity which consists of relatively less amino acids compared to traditional peptides which have more than 36 amino acids and forms a stable helical structure in an aqueous solution without necessitating complicated post-synthetic modifications.

SUMMARY OF THE INVENTION

To solve the above problems, the inventors of the present invention introduced a helix-capping motif into both N-terminus and C-terminus of a peptide derived from a C-terminal helical region of gp41 or substituted into amino acids that can facilitate the formation of a helical structure in order to stabilize a helical structure of a peptide and subsequently confirmed that the peptides can inhibit the cell fusion of HIV via a strong interaction with N-terminal helical region of gp41. The object of the present invention is to provide peptides that can inhibit the infection of HIV containing helix-capping motifs at both ends of a 19-mer peptide (628$^{th}$–646$^{th}$ region) derived from C-terminus of gp41, an envelope glycoprotein of HIV.

DETAILED DESCRIPTION OF THE INVENTION

The present invention relates to peptides that can inhibit HIV infection, wherein said peptides contain the 19-mer peptide($628^{th}$–$646^{th}$ amino acid region) derived from C-terminus of gp41 having helix-capping motifs at both ends of the peptide.

The present invention can be explained in more detail as follows.

As described earlier in 'Description of Related Art', Gp41 consists of a fusion peptide which exhibits an activity on cell membrane fusion, an N-terminal helical region, a C-terminal helical region, a transmembrane region, and a cytoplasmic region. Peptides derived from two helical regions of gp41 ectodomain can bind to each other in an aqueous solution, and form a very stable six helix bundle structure consisting of an internal triple-stranded coiled-coil core with three anti-parallel helices packing in the coiled-coil core. The above interaction then plays a crucial role in cell fusion activity as well as stabilizing the structure of gp41 protein, and any substance that can inhibit the above interaction will be able to inhibit both stability and function of gp41 thus resulting ii the inhibition of HIV infection and eventually being useful as a therapeutic agent for AIDS treatment. Based on the fact that WT (Table 1 and FIG. 1b: hydrophobic amino acids contacting the coiled-coil is placed at a and d positions), a peptide consisting of 19 amino acids as in SEQ ID NO. 4 of C-terminus ($628^{th}$–$646^{th}$ amino acid region) of gp41, is located on the central region of C-terminal helical region that strongly interacts with the N-terminal helical region, the present invention selectively introduced APKE and KQGI into the terminus of the peptide as helix-capping motifs to be linked to N-terminus and C-terminus represented by SEQ ID NO. 2 and SEQ ID NO. 3, respectively, and inhibit the interaction between the above two helical regions and thus enabling to inhibit the infection of HIV. In addition, the 19-mer peptide at C-terminus of gp41 ($628^{th}$–$646^{th}$ amino acid region) can be substituted for MT peptide or MT* peptide [Table 2 and FIG. 1c: 8 amino acids among those located at b, c, d, f positions can be substituted for other amino acids (alanine or lysine)] such as SEQ ID Nos. 5 and 6 that can form the helical structure from a given peptide. The examples of peptides that can be used to inhibit HIV infection are SEQ ID Nos. 7–13, wherein SEQ ID Nos. 11,12, 13 are the symmetrical bivalent peptides with a branched K of C-terminus, respectively. The amino acid sequences used in the present invention are abbreviated in accordance with IUPAC nomenclature as shown in the following Table 1.

TABLE 1

| Amino acid | Abbreviation |
|---|---|
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

This invention is explained in more detail based on the following Examples but they should not be construed as limiting the scope of this invention.

EXAMPLE

Synthesis of a Modified Peptide

Figure 1A:
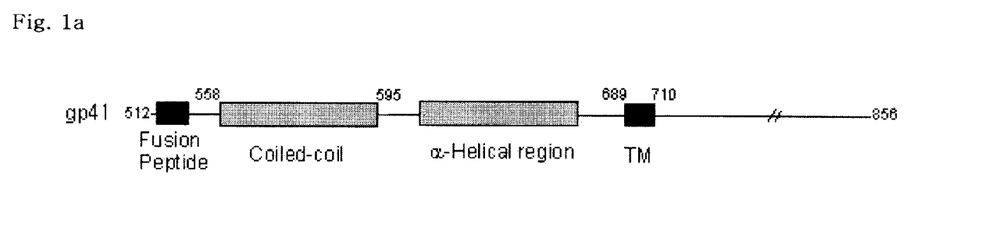
FIG. 1a shows a schematic representation of gp41 envelope glycoprotein of HIV.
Figure 1B:
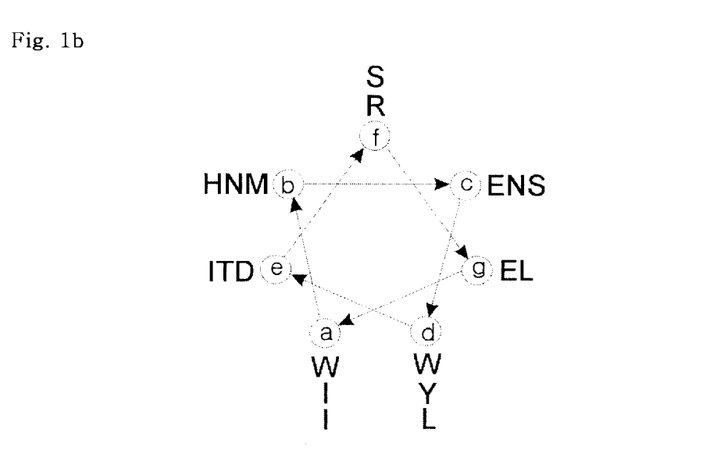
FIG. 1b shows the helical wheel representation of a wild type peptide.
Figure 1C:
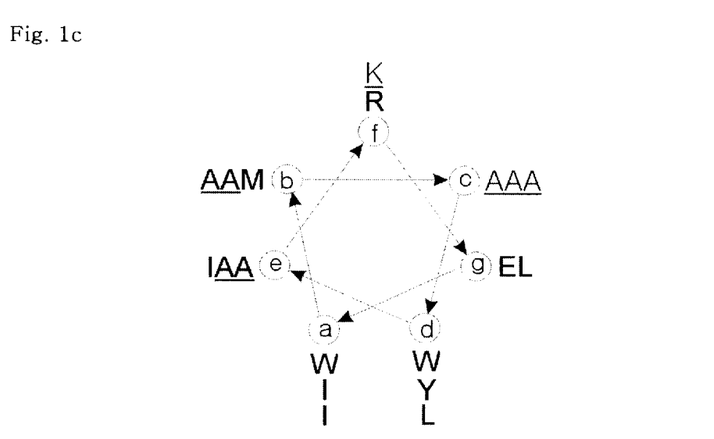
FIG. 1c shows the helical wheel representation of a mutant type peptide.

FIG. 1a shows a schematic diagram of gp41. WT, a peptide consisting of 19 amino acids at C-terminal helical region($626^{th}$–$646^{th}$ amino acid) of gp41, was used as a template in this experiment because it is located in the center of C-terminal helical region, which is known to have a strong interaction with the N-terminal helical region of gp41. The 19 amino acids of WT are shown in FIG. 1b in a helical wheel. Hydrophobic amino acids which can contact with the N-terminal helical region are located at 'a' and 'd' positions. For the MT peptide, eight amino acid residues at positions b, c, d and f were changed to other amino acids (either alanine or lysine) which can induce a helical structure (FIG. 1c). APKE and KQGI were used as N- and C-terminus helix-capping motifs respectively. Caps-MT* is a peptide wherein K, a positively charged amino acid, is replaced with E, a negatively charged amino acid, along with an introduction of an amino acid denoted as D. After introducing a helix-capping motif at N-terminus and a branch-type amino acid of K at C-terminus, branch-type peptide Ncap-MT * [BG1], Ncap-MT * [BG2], Ncap-MT * [BG3] were synthesized. A branch-type amino acid, Fmoc-Lys(Fmoc)-OH is coupled at the first reaction of peptide synthesis to produce a bivalent peptide. Thus, although branch-type peptide Ncap-MT * [BG1], Ncap-MT * [BG2], and Ncap-MT * [BG3] are actually 49-mer, 51-mer and 53-mer, respectively, their syntheses are achieved by the same method as in the synthesis of a non-branched type peptide and there requires no additional method to chemically link amino acid residues to make the designed branch-type peptide, and the cycle of peptide synthesis is the same as the non-branch type peptide. Designed peptides were synthesized by means of Fmoc method using Rink Amide MBHA resin and Fmoc-protected amino acids. Fmoc-Lys(Fmoc)-OH was used for a given branch-type peptide having a branch-type C-terminus and thus synthesized peptides resulted in having an amide at the C-terminus. Synthesized peptides were allowed to react in a mixture containing distilled water, phenol, thioanisol, and ethandithiol for 3 hr at room temperature and separated a given peptide from the resin. The separated peptides from the resin were washed 3 times with ether and further separated by reverse phase $C_{18}$ column, using an acetonitrile gradient in 0.1% trifluoroacetic acid solution. The identity of the purified peptides was confirmed by measuring their molecular masses by mass spectrometry, and the synthesized peptides are shown in the following Table 2.

TABLE 2

| Peptides | Amino Acid Sequence | SEQ ID NO. |
|---|---|---|
| WT | WMEWDREINNYTSLIHSLI | 4 |
| MT | WMaWaREIaaYakLIaaLI | 5 |
| MT* | WMEWDaEIaaYTELIaaLI | 6 |
| Ncap-MT | APKEWMaWaREIaaYakLIaaLI | 7 |
| Caps-WT | APKEWMEWDREINNYTSLIHSLIKQGI | 8 |
| Caps-MT | APKEWMaWaREIaaYakLIaaLIKQGI | 9 |
| Caps-MT* | APKEWMEWDaEIaaYTELIaaLIKQGI | 10 |
| Ncap-MT*[BG1] | (APKEWMEWDaEIaaYTELIaaLIG)$_2$K$^{(3)}$ | 11 |
| Ncap-MT*[BG2] | (APKEWMEWDaEIaaYTELIaaLIGG)$_2$K$^{(3)}$ | 12 |
| Ncap-MT*[BG3] | (APKEWMEWDaEIaaYTELIaaLIGGG)$_2$K$^{(3)}$ | 13 |

N.B.
[1] Lower case letters represent substituted amino acids.
[2] Helix-capping motifs are underlined.
[3] Italic K, K, represent Fmoc-Lys(Fmoc)-OH type of an amino acid introduced to form a symmetrical bivalent peptide.

EXPERIMENTAL EXAMPLE 1

Analyses of Secondary Structures of Synthesized Peptides (1) Analyses of Secondary Structures of Peptides in Phosphate Buffered Saline (PBS)

Figure 2A:
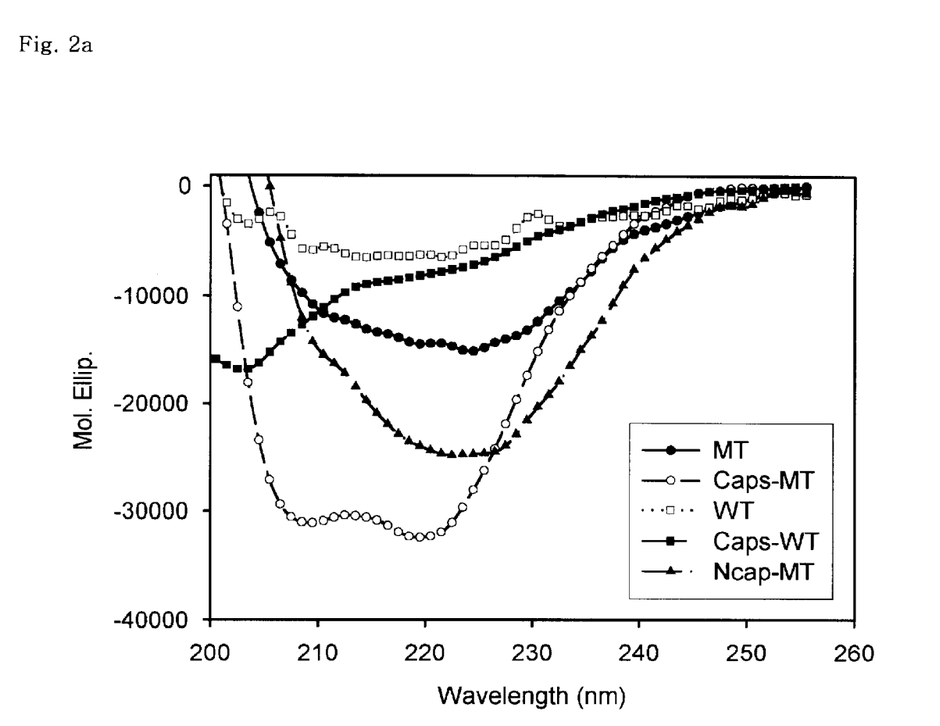
FIG. 2a shows circular dichroism spectra of peptides in a phosphate saline buffer.

The secondary structures of peptides synthesized in the above Example were analyzed by means of circular dichroism and the circular dichroism spectra of synthesized peptides were analyzed by using 715 CD spectropolarimeter (Jasco Co., Ltd., JAPAN). The peptides of WT(SEQ ID NO. 4), MT(SEQ ID NO. 5), Ncap-MT(SEQ ID NO. 7), Caps-WT(SEQ ID NO. 8), Caps-MT(SEQ ID NO. 9) were dissolved in PBS(pH 7.0) with 100 mM sodium phosphate and 150 mM NaCl to make the final concentration of each peptide 50 $\mu$M and were placed for spectrum analyses. The results are shown in FIG. 2a.

Figure 2B:
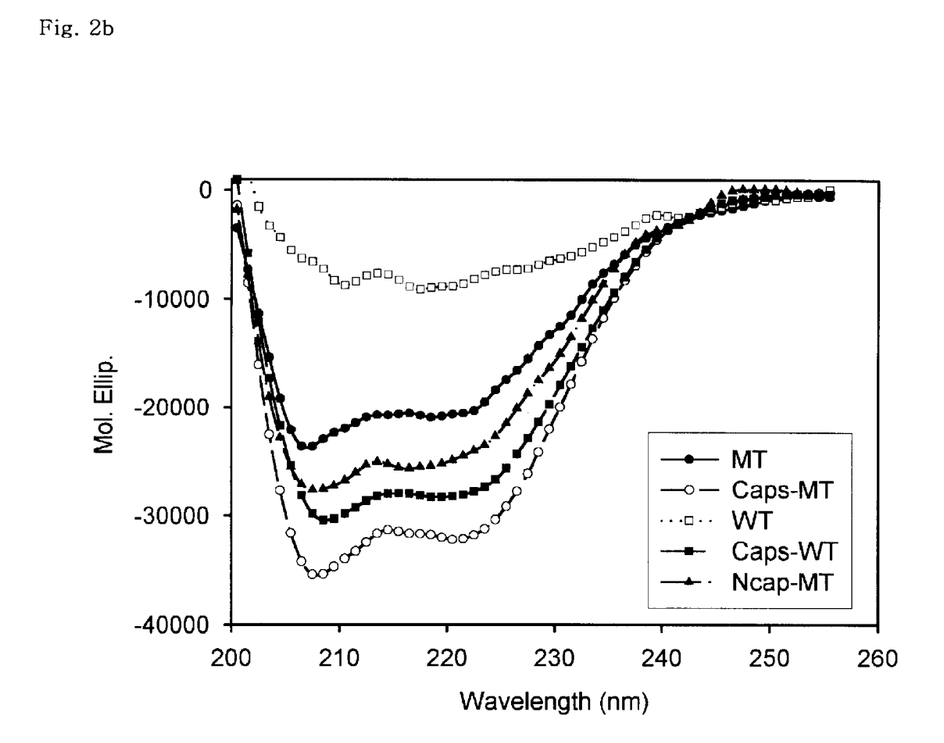
FIG. 2b shows circular dichroism spectra of peptides in a phosphate saline buffer containing a 30% trifluoroethanol.

(2) Analyses of Secondary Structures of Peptides in Phosphate Buffered Saline (PBS) containing Trifluoroethanol Experiments were performed the same as described in the above Experimental Example 1 (1) with the exception that the PBS contained 30% trifluoroethanol. The results of spectra analyses are shown in FIG. 2b.

EXPERIMENTAL EXAMPLE 2

Inhibitory Activity of Synthesized Peptides Against the Binding between Trx-N(N-terminal Helical Region of gp41) and GST-C(C-terminal Helical Region of gp41)

(1) Inhibitory Activity of Caps-MT*

Enzyme linked immunosorbent assay(ELISA) was employed to measure the level of inhibitory activity of peptides against the interaction between N- and C-terminal helical regions of gp41 (Ryu et al., Mol Cells, 8, 717–723, 1998). 0.1 mL of 0.001 mg/mL Trx-N (Thioredoxin-N-terminal), a thioredoxin containing the coiled-coil motif of gp41 at the C-terminus, was independently placed on the surface of each well of a 96-well plastic cell culture container for 12 hr for adsorption. After protein solutions were removed from each well, each well was treated with 0.3 mL 10 mM Tris-Cl (pH 8.0) containing 5% skim milk and placed at room temperature for 1 hr. Then, they were washed with PBST solution [100 mM $NaPO_4$, 150 mM NaCl (pH 7.0), 0.5% Tween 20] 6 times and allowed to react for 1 hr at room temperature with a mixture containing 0.1 mL of 0.001 mg/mL GST-C (Glutathione S-Transferase-C-terminus) and various concentrations of up to ~10 $\mu$M of peptide Caps-MT*. After they were removed from the wells, they were then washed 6 times with a PBST solution, added with 0.1 mL of anti-GST antibodies, i.e., primary antibodies, which were diluted 1/2000 in PBS, and were allowed to react for 1 hr. After removing the antibody-containing solution, the mixture was again washed 6 times with a PBST solution, added with 0.1 mL of anti-Goat antibodies recognizing anti-GST antibodies, i.e., secondary antibodies, which were diluted 1/2000 in PBS, and were allowed to react for 1 hr. After removing the antibody-containing solution, the mixture was again washed 6 times with a PBST solution 1 mL of peroxidase containing 1 mg/mL of OPD (o-Phenylenediamine dihydrocliloride) to react for 5 min, added with 0.1 mL of 2.5 M sulfuric acid to terminate the reaction, and the absorbance was measured at 490 nm. The results are summarized in FIG. 3.

(2) Inhibitory Activity of Ncap-MT*[BG2]

Figure 3:
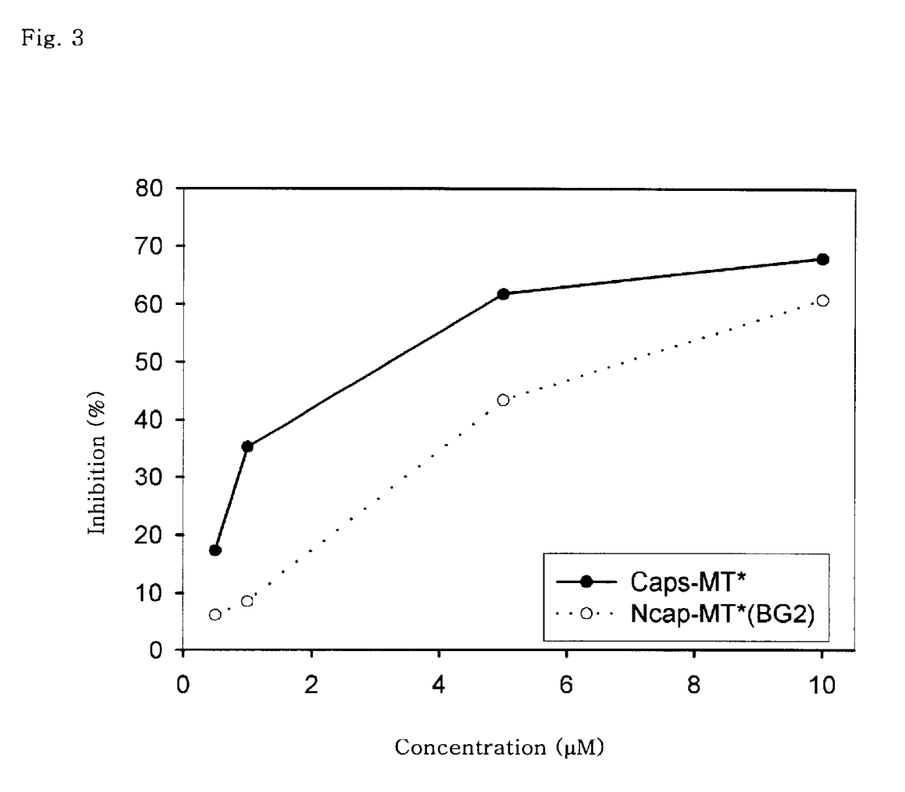
FIG. 3 shows the inhibitory activity of a peptide against the interaction between N- and C-terminal helical regions of gp41 by ELISA assay.

The experiments were performed the same as described in the above Experimental Example 2 (1) for Caps-MT* with the exception that a mixture containing 0.1 mL of 0.001 mg/mL GST-C and various concentrations of up to 10 $\mu$M of peptide Ncap-MT*[BG2] was used instead of a mixture containing 0.1 mL of 0.001 mg/mL GST-C and various concentrations of up to 10 $\mu$M of peptide Caps-MT*. The absorbance was also measured as in the above (1). The results are shown in FIG. 3.

EXPERIMENTAL EXAMPLE 3

The Binding Affinity of Synthesized Peptides in the Example for Trx-N, Thioredoxin Containing N-terminal Helical Region of gp41

(1) The Binding Affinity of Caps-WT peptide

Figure 4A:
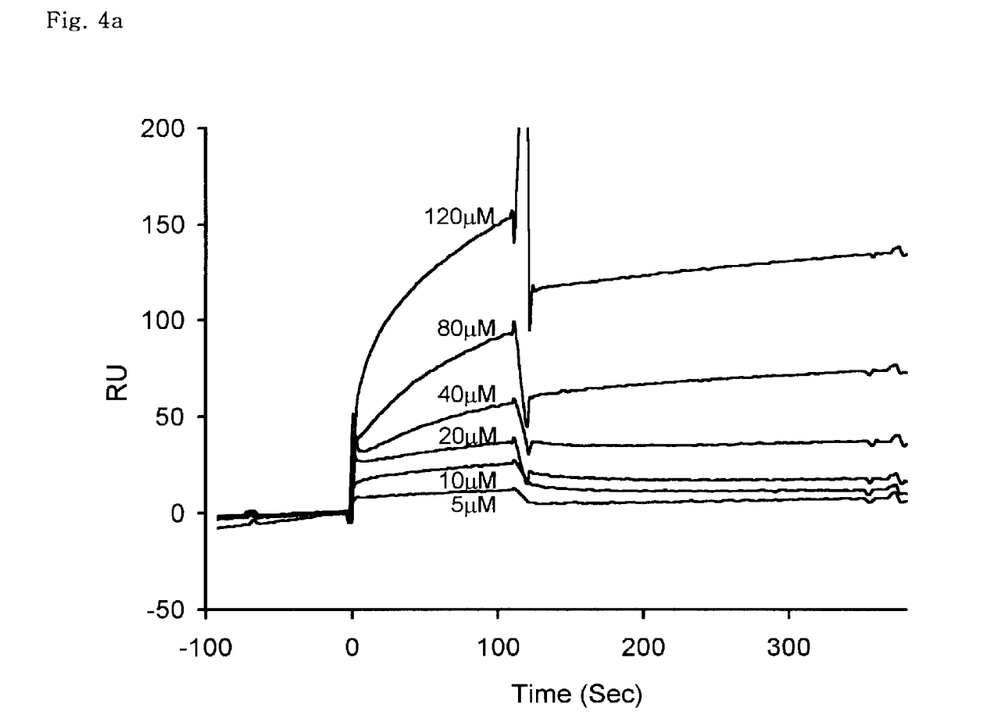
FIG. 4 shows binding sensorgrams of peptides to Trx-N by a BIAcore instrument.

BIAcore2000 was used to measure the binding affinity of peptides for the N-terminal helical region of HIV gp41. Trx-N and Trx proteins were immobilized at the separate channels of CM5 sensor chip, respectively, in which the dextran surface of channels of a CM5 sensor chip was activated with EDC/NHS [N'-(3-dimethylaminopropyl) carbodiimidehydrochloride/ N-hydroxysuccininmide], flowing 0.2 mg/mL of Trx-N and Trx at the rate of 0.005 mg/mL into a CM5 sensor chip. The dextran surfaces where proteins had not been adsorbed were deactivated by using 0.005 mg/mL of ethanolamine. Association sensorgram was confirmed by flowing each dilution of Caps-WT, a synthesized peptide in PBS into 5 $\mu$M, 10 $\mu$M, 20 $\mu$M, 40 $\mu$M, 80 $\mu$M, and 120 $\mu$M, respectively, into each sensor channel. Dissociation sensorgram was obtained by flowing a PBS buffer solution. Non-specific binding was corrected by subtracting Trx sensorgram from Trx-N sensorgram. The association/dissociation sensorgram of peptides are summarized in FIG. 4a.

(2) The Binding Affinity of WT peptide

Figure 4B:
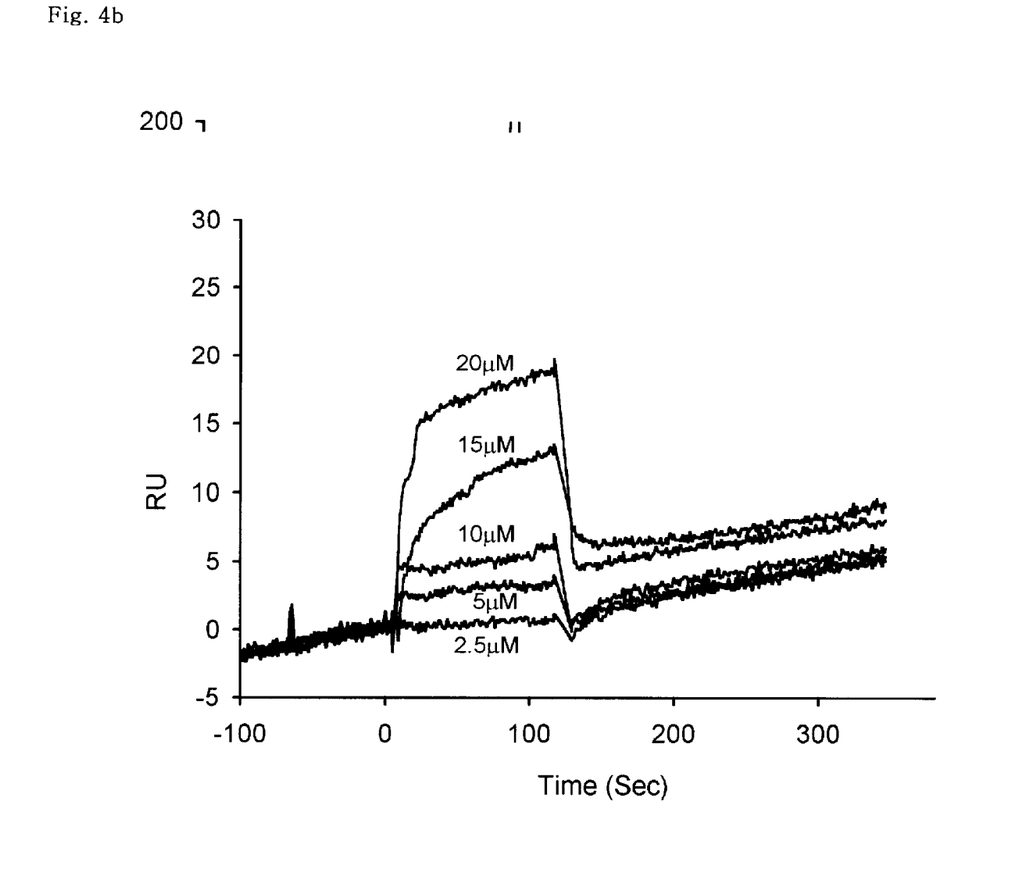

Experiments were performed the same as in the above Experimental Example 3 (1) for Caps-WT peptide with the exception that the peptide used was WT and it was diluted in PBS into 2.5 $\mu$M, 5 $\mu$M, 10 $\mu$M, 15 $\mu$M, and 20 $\mu$M, respectively. The resulting association/dissociation sensorgrams of peptides are summarized in FIG. 4b.

(3) The Binding Affinity of MT peptide

Figure 4C:
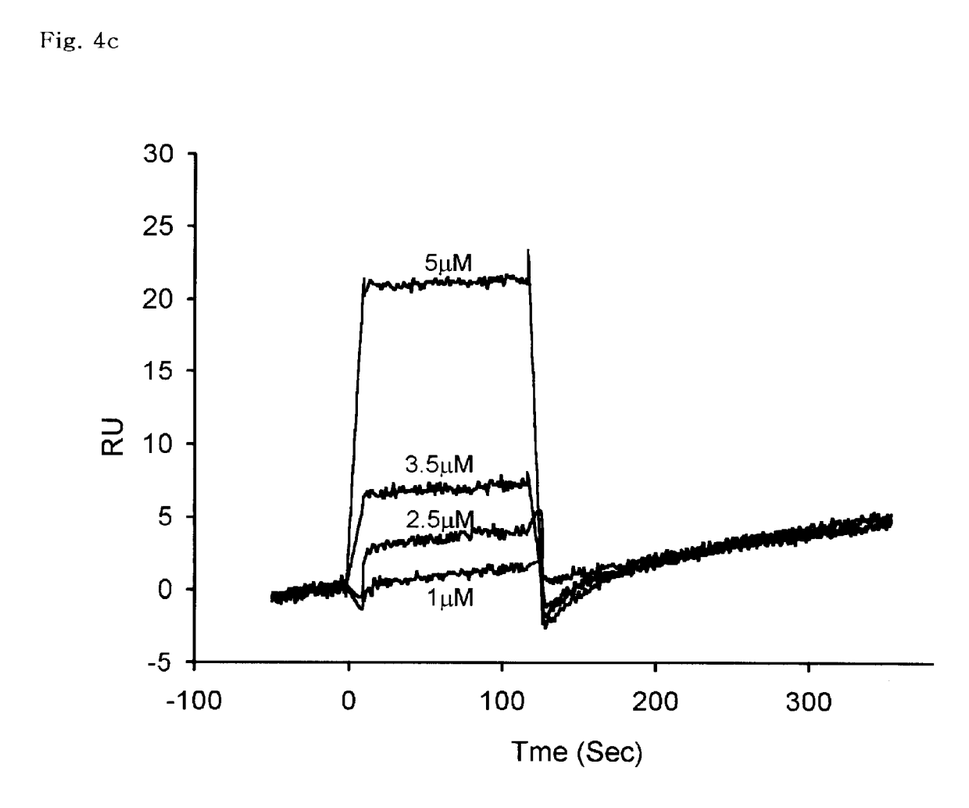

Experiments were performed the same as in the above Experimental Example 3 (1) for Caps-WT peptide with the exception that the peptide used was MT and it was diluted in PBS into 1 $\mu$M, 2.5 $\mu$M, 3.5 $\mu$M, and 5 $\mu$M, respectively. The resulting association/dissociation sensorgrams of peptides are summarized in FIG. 4c.

(4) The Binding affinity of DP 178 peptide

Figure 4D:
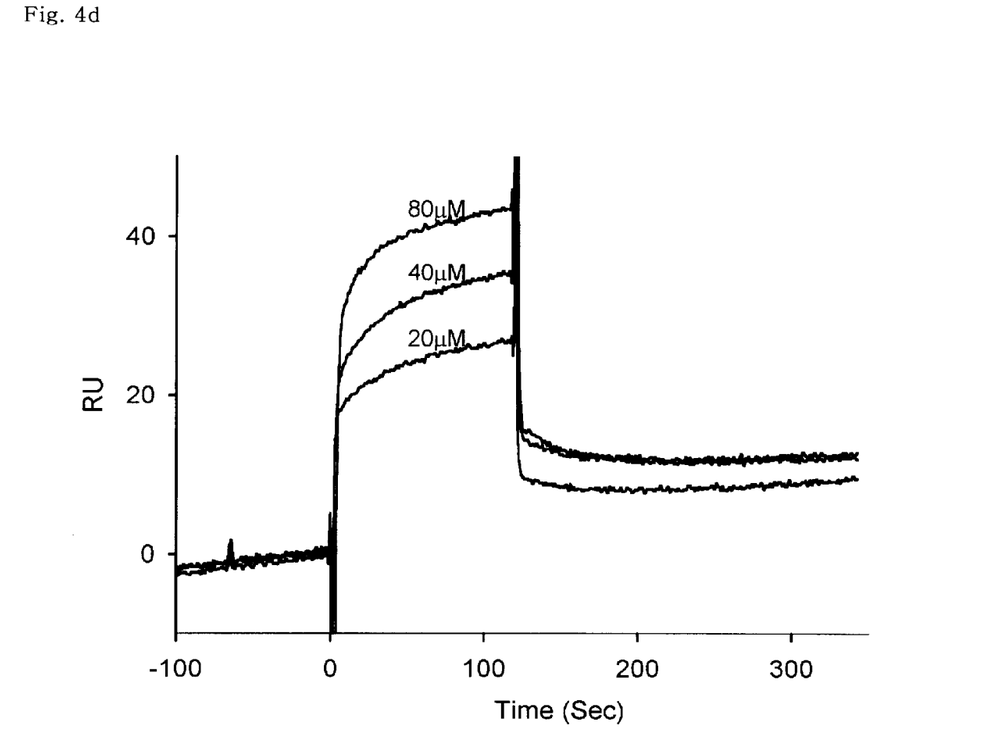

Experiments were performed the same as in the above Experimental Example 3 (1) for Caps-WT peptide with the exception that the peptide used was DP178 and it was diluted in PBS into 20 $\mu$M, 40 $\mu$M, 80 $\mu$M, respectively. The resulting association/dissociation sensorgrams of peptides are summarized in FIG. 4d.

(5) The Binding Affinity of Ncap-MT peptide

Figure 4E:
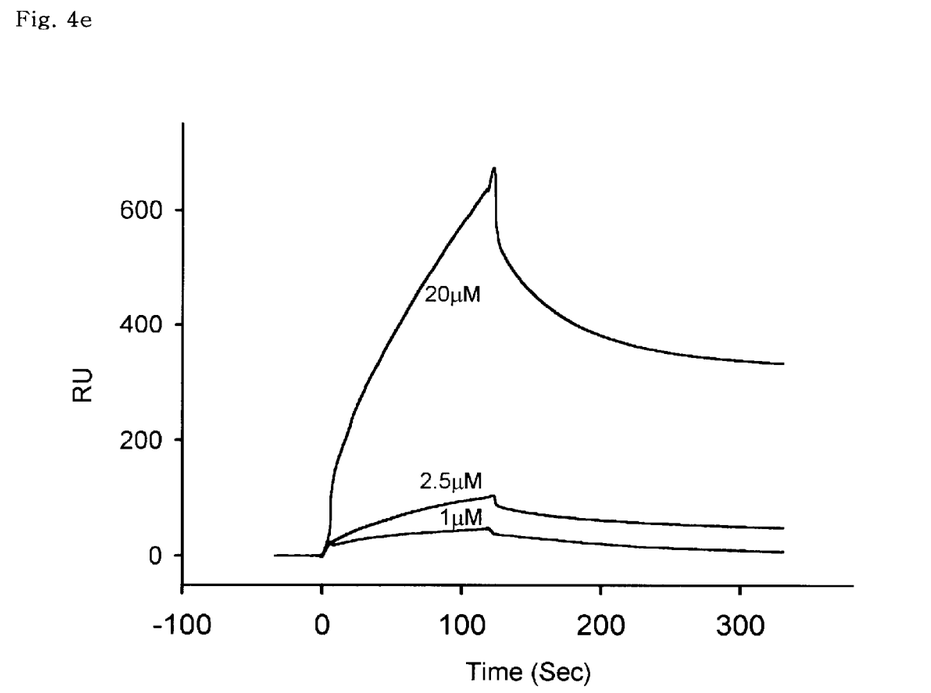

Experiments were performed the same as in the above Experimental Example 3 (1) for Caps-WT peptide with the exception that the peptide used was Ncap-MT and it was diluted in PBS into 1 $\mu$M, 2.5 $\mu$M, and 20 $\mu$M, respectively. The resulting association/dissociation sensorgrams of peptides are summarized in FIG. 4e.

(6) The Binding Affinity of Caps-MT peptide

Figure 4F:
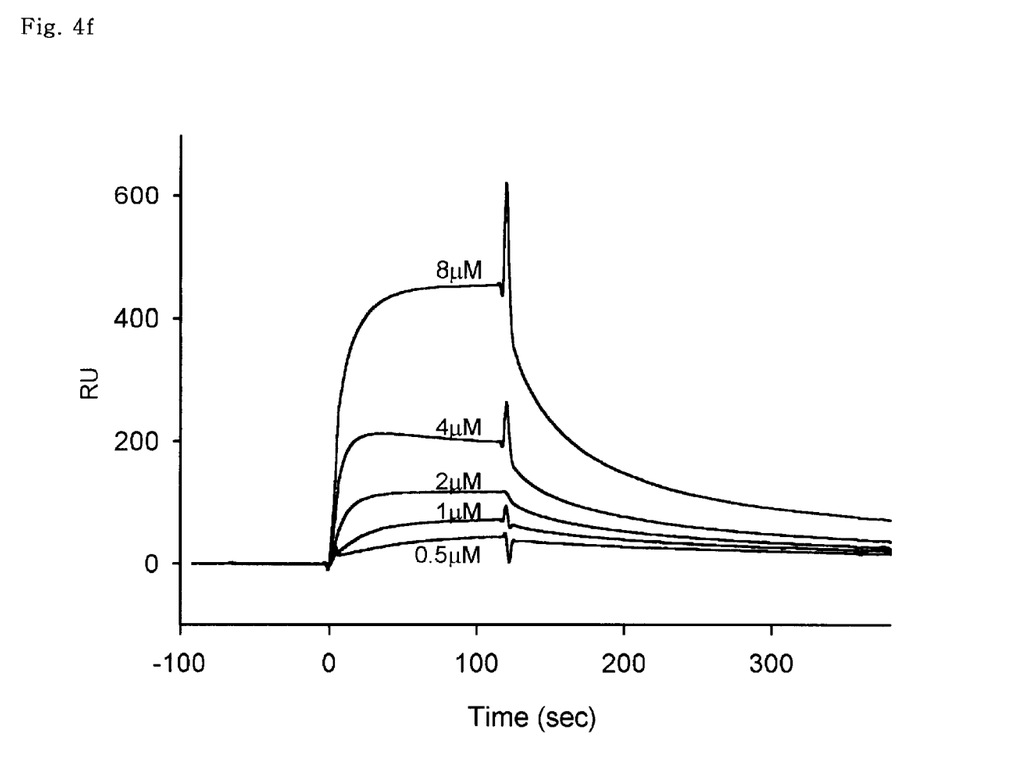

Experiments were performed the same as in the above Experimental Example 3 (1) for Caps-WT peptide with the exception that the peptide used was Caps-MT and it was diluted in PBS into 0.5 $\mu$M, 1 $\mu$M, 2 $\mu$M, 4 $\mu$M, and 8 $\mu$M, respectively. The resulting association/dissociation sensorgrams of peptides are summarized in FIG. 4f.

EXPERIMENTAL EXAMPLE 4

Figure 5:
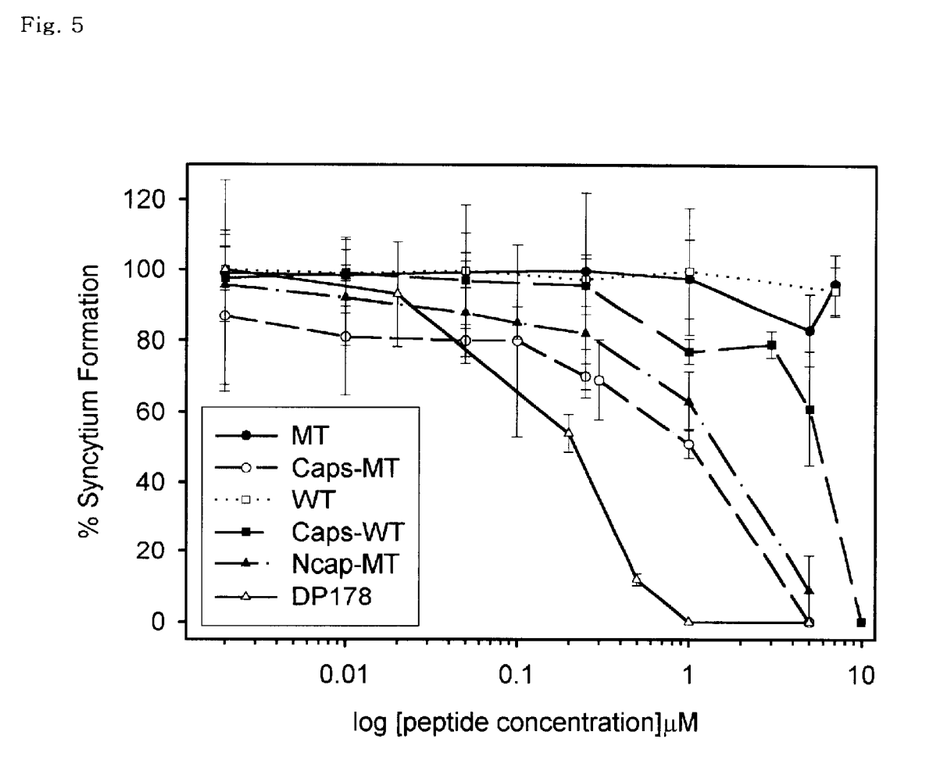
FIG. 5 shows the inhibitory activity of peptides against the gp41-mediated cell fusion.

Inhibitory Activity of Synthesized Peptides Against Cell Fusion Mediated by gp41 of HIV (1) Inhibitory Activity of MT peptide against Cell Fusion The anti-gp41 activity of MT peptide was examined by measuring its inhibitory activity against gp41-mediated cell fusion, using CD4 HeLa cells and vaccinia virus expressing gp120/gp41 envelope glycoprotein of HIV-1 (Woo et al., Phytomedicine, 4, 53–58, 1997). $1 \times 10^3$ of log phase CD4-HeLa cells were diluted in ham F12 solution—a mixture of 10% newborn calf serum inactivated by heat treatment, penicillin, and streptomycin—and then cultured in a 12-well cell culture container for 3 days. Then, MT peptide was diluted in 0.2 mL of ham F12 solution to be 0.002 µM, 0.01 µM, 0.05 µM, 0.35 µM, 1 µM, 5 µM, 7 µM, and then introduced into a HeLa cell, respectively, and cultured for 30 min. And then $7.3 \times 10^2$ pfu of vaccinia virus were diluted in 0.8 L of ham F12 solution and added into a pretreated HeLa cell and cultured for one day. The number of nuclei in fused cells were compared between the cells with treated peptides and those with untreated, and the resulting inhibitory activities measured are shown in the FIG. 5.

(2) Inhibitory Activity of Caps-MT peptide against Cell Fusion

Experiments were performed the same as in the above Experimental Example 4 (1) for MT peptide with the exception that the peptide used was Caps-MT and it was diluted in 0.2 mL of ham F12 into 0.002 µM, 0.01 µM, 0.05 µM, 0.1 µM, 0.25 µM, 0.3 µM, 1 µM, and 5 µM, respectively. The resulting inhibitory activities measured are shown in the FIG. 5.

(3) Inhibitory Activity of WT peptide against Cell Fusion

Experiments were performed the same as in the above Experimental Example 4 (1) for MT peptide with the exception that the peptide used was WT and it was diluted in 0.2 mL of ham F12 into 0.002 µM, 0.01 µM, 0.05 µM, 0.25 µM, 1µM and 7 µM, respectively. The resulting inhibitory activities measured are shown in the FIG. 5.

(4) Inhibitory Activity of Caps-WT peptide against Cell Fusion

Experiments were performed the same as in the above Experimental Example 4 (1) for MT peptide with the exception that the peptide used was Caps-WT and it was diluted in 0.2 mL of ham F12 into 0.002 µM, 0.01 µM, 0.05 µM, 0.25 µM, 1 µM, 3 µM, 5 µM and 10 µM, respectively. The resulting inhibitory activities measured are shown in the FIG. 5.

(5) Inhibitory Activity of Ncap-MT peptide against Cell Fusion

Experiments were performed the same as in the above Experimental Example 4 (1) for MT peptide with the exception that the peptide used was Ncap-MT and it was diluted in 0.2 mL of ham F12 into 0.002 µM, 0.01 µM, 0.05 µM, 0.1 µM, 0.25 µM, 1 µM, and 5 µM, respectively. The resulting inhibitory activities measured are shown in the FIG. 5.

(6) Inhibitory Activity of DP178 peptide against Cell Fusion

Experiments were performed the same as in the above Experimental Example 4 (1) for MT peptide with the exception that the peptide used was DP178 and it was diluted in 0.2 mL of ham F12 into 0.002 µM, 0.02 µM, 0.2 µM, 0.5 µM, 1 µM, and 5 µM, respectively. The resulting inhibitory activities measured are shown in the FIG. 5.

As described in the above, the present invention relates to peptides which can prevent the infection of HIV via the inhibition of gp41, and it was found that the anti-gp41 activity of the peptide is directly proportional to its binding affinity for the coiled-coil region of gp41 and the helical content of the peptide as shown in the following Table 3.

TABLE 3

| Peptide | $K_D(M)$[1] | Helical content (%) | | $IC_{50}(\mu M)$[3] |
| --- | --- | --- | --- | --- |
| | | PBS | 30% TFE[2] | |
| WT | — | 18 | 24 | ND[4] |
| MT | — | 42 | 59 | ND[4] |
| Caps-WT | $1.3 \times 10^{-6}$ | 21 | 77 | 5.8 |
| Ncap-MT | $8.9 \times 10^{-7}$ | 69 | 68 | 1.7 |
| Caps-MT | $2.9 \times 10^{-7}$ | 87 | 88 | 1.0 |

[1] $K_D(M)$: the apparent dissociation constant of the peptide on Trx-N, defined as $k_{dissociation}/k_{association}$ for each peptide.
[2] TFE: trifluoroehtanol
[3] $IC_{50}(\mu M)$: peptide concentration that cell fusion is inhibited 50%
[4] ND: not determined Consequently, the peptides prepared according to the present invention can inhibit the cell fusion of HIV and the relatively short length of the above peptides consisting of less than 30 amino acids, as compared to those of previous anti-HIV peptides consisting of more than 36 amino acids, can reduce the ultimate cost of unit production as well as the difficulty in synthesis of these peptides, can allow mass production, and the relatively stable secondary structure of the peptides after synthesis also do not necessitate any particular modifications.

---

What is claimed is:

1. A peptide that can inhibit the infection of HIV, wherein said peptide comprises:
   i) 19 amino acids ($628^{th}$–$646^{th}$ region) of C-terminal helical region of gp41, or
   ii) 19 amino acids ($628^{th}$–$646^{th}$ region) of C-terminal helical region of gp41,
   wherein at least one amino acid has been mutated from the wild type sequence in order to promote a helical structure in the peptide,
   and helix-capping motifs appended to at least one end of the peptide, wherein the peptide is chosen from:
   a) a peptide consisting of from 19 to 27 amino acids; and
   b) a bivalent peptide with two symmetrical halves each consisting of from 24 to 26 amino acids, joined by an amino acid.

2. The peptides that can inhibit the infection of HIV in accordance with claim 1, wherein sequences of helix-capping motifs of said peptides are represented by either SEQ ID NO. 2 or SEQ ID NO. 3.

3. The peptides that can inhibit HIV infection in accordance with claim 1 or claim 2, wherein said 19 amino acids of C-terminus of gp41 of HIV at its 628$^{th}$–646$^{th}$ region is selected from a group consisting of SEQ ID NOs. 4, 5 and 6.

4. The peptides that can inhibit HIV infection in accordance with claim 3, wherein said peptides are selected from the group consisting of SEQ ID NOs. 7, 8, 9, 10, 11, 12 and 13, wherein SEQ ID NOs. 11, 12 and 13 have a branched K at C-terminus of peptides, respectively.

* * * * *